(12) United States Patent
Sun

(10) Patent No.: US 10,668,079 B2
(45) Date of Patent: Jun. 2, 2020

(54) COMPOSITION COMPOSED OF CEFTRIAXONE SODIUM AND SULBACTUM SODIUM

(71) Applicants: XIANGBEI WELMAN PHARMACEUTICAL CO., LTD., Hunan (CN); GUANGZHOU WELMAN NEW DRUG R&D CO., LTD., Guangdong (CN); NANJING KANGFUSHUN PHARMACEUTICAL CO., LTD., Jiangsu (CN)

(72) Inventor: Mingjie Sun, Hunan (CN)

(73) Assignees: XIANGBEI WELMAN PHARMACEUTICAL CO., LTD., Hunan (CN); GUANGZHOU WELMAN NEW DRUG R&D CO., LTD., Guangdong (CN); NANJING KANGFUSHUN PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 16/093,685

(22) PCT Filed: Nov. 2, 2016

(86) PCT No.: PCT/CN2016/104327
§ 371 (c)(1),
(2) Date: Oct. 15, 2018

(87) PCT Pub. No.: WO2018/081944
PCT Pub. Date: May 11, 2018

(65) Prior Publication Data
US 2019/0125755 A1    May 2, 2019

(51) Int. Cl.
*A61K 31/546*    (2006.01)
*A61P 31/04*    (2006.01)
*A61K 31/43*    (2006.01)
*A61K 9/00*    (2006.01)
*A61K 9/19*    (2006.01)
*A61K 9/14*    (2006.01)
*C07D 201/00*    (2006.01)
*A61K 9/08*    (2006.01)

(52) U.S. Cl.
CPC .......... *A61K 31/546* (2013.01); *A61K 9/0019* (2013.01); *A61K 9/08* (2013.01); *A61K 9/14* (2013.01); *A61K 9/19* (2013.01); *A61K 31/43* (2013.01); *A61P 31/04* (2018.01); *C07D 201/00* (2013.01)

(58) Field of Classification Search
CPC .. A61K 2300/00; A61K 31/43; A61K 31/546; A61K 9/0019; A61K 9/14; A61K 9/19; A61K 9/08; A61P 31/04; C07D 201/00
See application file for complete search history.

(56) References Cited

FOREIGN PATENT DOCUMENTS

| CN | 101648016 A | 2/2010 |
|---|---|---|
| CN | 102462684 A | 5/2012 |
| CN | 102993215 A | 3/2013 |
| CN | 103113390 A | 5/2013 |
| WO | 2006059344 A1 | 6/2006 |
| WO | 2014/040280 A1 | 3/2014 |

OTHER PUBLICATIONS

Chun tao et al.: Chinese Journal of Antibiotics (2007, 32 (11) 672-678.
Xue Jing1, et al.; Acta Pharmaceutica Sinica (corresponding to "Pharmaceutical Journal" as cited in the specification of the present application) (2014, 49 (7) 1034-1038).
Brenner et al: Biochemistry 1981, 20, 3680-3687.
Author unkown: "Influence of Reaction Solvent on Crystalline State of Sulbactam Sodium", J Huaihai Med. 2005, 23 (5) 423.
Author unkown: Provisions for Drug Registration (SFDA Order No. 28) pp. 1-20, downloaded from http://eng.sfda.gov.cn/WS03/CL0768/61645.html on Nov. 2, 2018.
Author unkown: Drug Administration Law of the People's Republic of China; Order of the President of the Peoples Republic of China (No. 45); pp. 1-13; downloaded from the internet http://eng.sfda.gov.cn/WS03/CL0766/61638.html dated Nov. 2, 2018.
Author unkown: Good Manufacturing Practice for Drugs (2010 Revision) ( MOH Decree No. 79 ); pp. 1-39; downloaded from the Internet http://eng.sfda.gov.cn/WS03/CL0768/65113.html on Nov. 2, 2018.
Author unkown: Chinese Pharmacopoeia 2015—Guiding Principles (pp. 2-11) (with English Abstract); 2015.
Author unkown: Physical Tests / (941) X-Ray Powder Diffraction pp. 427-433.
Author unkown: European Pharmacopoeia 8.0 (Ceftriaxone sodium) pp. 1-3.
Author unkown: European Pharmacopoeia 8.0 (Sulbactam sodium) pp. 1-3.
Author unkown: Chinese Pharmacopoeia 2015—Examination method of Clarity, pp. 1-3.
Author unkown: China Tropical Medicine, 2010, 10(8), 946-948, pp. 1-4.

*Primary Examiner* — Robert A Wax
*Assistant Examiner* — Olga V. Tcherkasskaya
(74) *Attorney, Agent, or Firm* — Millen White Zelano and Branigan, PC; John Sopp

(57) ABSTRACT

The present disclosure provides a composition consisting of ceftriaxone sodium and sulbactam sodium, a pharmaceutical formulation comprising the same and the application thereof. The composition is characterized by having an X-ray powder diffraction pattern with peaks at specific angles. The pharmaceutical formulation according to the present disclosure have better antibacterial activity and stability compared with known compositions, and are thus very suitable for the treatment of bacterial infections, especially for the treatment of refractory urogenital system infections caused by *Neisseria gonorrhoeae* which has drug-resistance to a variety of antibiotics (β-lactams, tetracyclines, macrolides, fluoroquinolones and aminoglycosides).

20 Claims, 8 Drawing Sheets

COMPOSITION COMPOSED OF CEFTRIAXONE SODIUM AND SULBACTUM SODIUM

TECHNICAL FIELD

The present disclosure relates to a composition, and particularly relates to a composition consisting of ceftriaxone sodium and sulbactam sodium. The present disclosure also relates to a pharmaceutical formulation comprising the composition and use thereof.

BACKGROUND

Ceftriaxone is a third-generation cephalosporin antibiotic and its sodium salt is commonly used in clinical practice. Ceftriaxone sodium has great antibacterial activity against a variety of gram-negative bacteria and some gram-positive bacteria (such as *Escherichia coli, Klebsiella pneumoniae, Neisseria gonorrhoeae* and the like), and can be used for the treatment of infectious diseases caused by sensitive bacteria. However, there is a certain limit on the application of ceftriaxone sodium due to its insensitivity to Methicillin-Resistant *Staphylococcus aureus* (MRSA) and *Enterobacter cloacae*. Sulbactam is a β-lactamase inhibitor. In the prior art, sulbactam sodium and ceftriaxone sodium are formulated into a compound formulation, which improves the antimicrobial spectrum and sensitivity of ceftriaxone to drug-resistant bacteria.

Stable quality of a drug is critical for ensuring the safety of drug use. The crystalline form (crystalline morphology) of a crude drug plays a very important role in stabilizing the drug quality. Regarding the quality control of a drug, different crystalline forms (crystalline morphologies) of the drug may have different stability and thus affect the drug quality. If the crystalline form (crystalline morphology) of a drug is determined, the quality of the drug would be more stable and be easier to be controlled; otherwise, the drug quality would vary from batch to batch, resulting in different stability of different batches.

Prior research showed that ceftriaxone sodium can have many different crystalline morphologies. A single crystal structure of ceftriaxone sodium was simulated by means of a software, and provides useful reference for researchers on the crystal of ceftriaxone sodium. Ceftriaxone sodium has three sub-crystalline forms which have differences in all the following aspects: salt-forming rate, crystallinity, compatibility with butyl rubber closures and the like. These sub-crystalline forms of ceftriaxone sodium probably affect the efficacy of drugs.

Sulbactam sodium is also a substance which may be present in different crystalline forms. Sulbactam sodium may be crystallized from a mixed solvent of ethyl acetate and n-butanol, and its single crystal structure is also disclosed. Sulbactam sodium was prepared by using different solvents such as acetone, ethyl acetate, methanol, ethanol and the like, resulting in four different kinds of crystal which varied significantly in morphology, density and flowability. A sulbactam crystal can be formed, and the content of sulbactam can be maintained within 24 months.

In order to obtain pharmaceutical compound formulations of ceftriaxone sodium and sulbactam sodium with better efficacy as compared with single prescription preparations, it is necessarily required that the pharmaceutical compound formulations have stable quality. However, the compound formulations show greater complexity in the respect of preparation, efficacy and the like, as compared with the single prescription preparations. In the respect of crystalline form, both ceftriaxone sodium and sulbactam sodium have multiple different crystals as shown in the prior art, which results in the complexity of the crystalline form of the compound drug. Further, the preparation of the compound drug may also have an unpredictable effect on the crystal production of ceftriaxone sodium and sulbactam sodium.

Studies have found that the known compound preparations of ceftriaxone sodium and sulbactam sodium have unstable crystalline forms.

Under a condition of low temperature and inert gas, ceftriaxone sodium, sulbactam sodium and a lyoprotectant were dissolved in 70% ethanol to form a solution; the solution was added with a pH adjusting agent and subjected to lyophilization to form a eutectic powder, in which the active ingredient substantially did not degrade within 36 months. However, the eutectic powder comprised many components such as ceftriaxone sodium, sulbactam sodium, a lyoprotectant, a pH adjusting agent and the like, which might have certain effect on the crude drug itself. Studies have shown that the eutectic powder had a stable content, but had no stable crystal formed therein, which means that it was still unstable in the sense of crystallography.

Crystal is a substance in which the particles are arranged in an ordered microscopic structure. While the presence mode of the crystal cannot be predicted effectively, due to the limitations of scientific and technological level nowadays. Inventors expect to improve the quality of product, lengthen the shelf life, and improve the economy and safety of the compound formulation of ceftriaxone sodium and sulbactam sodium through in-depth research.

SUMMARY OF THE INVENTION

One of the objects of the present disclosure is to provide a stable composition consisting of ceftriaxone sodium and sulbactam sodium so as to solve the existing problems in the prior art such as poor stability, poor efficacy, short shelf life and the like.

A further object of the present disclosure is to provide a pharmaceutical formulation comprising a stable composition consisting of ceftriaxone sodium and sulbactam sodium.

A further object of the present disclosure is to provide use of said pharmaceutical formulation in the preparation of antibacterial drug.

When conducting studies on stability, the inventors found that, after 30 months of storage, the compound formulation of ceftriaxone sodium and sulbactam sodium showed slightly turbid after dissolving in water. When the preparation process of the compound formulation was further repeated, it was found that the crystalline form of the products had some problems: although the raw materials ceftriaxone sodium and sulbactam sodium had certain crystalline forms, the prepared compound formulation was amorphous. The instability of the crystalline forms may be one of the reasons leading to the turbidity of the compound formulation after long time storage.

For improving the preparation process of the compound formulation, the inventors surprisingly obtained a composition of ceftriaxone sodium and sulbactam sodium having specific crystal morphology.

According to one embodiment of the present disclosure, a composition consisting of ceftriaxone sodium and sulbactam sodium is provided, wherein the composition may have an X-ray powder diffraction pattern with peaks at 2θ±0.2° values 11.2, 14.3, 17.8, 19.3, 21.2, 22.8 and 23.8.

Preferably, the composition according to the present disclosure may further have an X-ray powder diffraction pattern with peaks at 2θ±0.2° values 12.6, 16.7, 18.4, 20.0, 20.4 and 28.0.

According to another embodiment of the present disclosure, a composition consisting of ceftriaxone sodium and sulbactam sodium may be provided, wherein the composition may have an X-ray powder diffraction pattern with the following interplanar crystal spacing values ±0.2 Å: 7.9, 6.2, 5.0, 4.6, 4.2, 3.9 and 3.7.

Preferably, the composition according to the present disclosure may further have an X-ray powder diffraction pattern with the following interplanar crystal spacing values ±0.2 Å: 7.1, 5.3, 4.8, 4.4, 4.3 and 3.2.

The composition according to the present disclosure is a crystalline substance (crystal). X-ray powder diffraction analysis is an authoritative means for identifying crystals in the art. Generally, the characteristics of the crystal may be better reflected by peaks at the low 2θ angle, at high interplanar crystal spacing, having a clear and complete morphology, and higher intensity in the obtained X-ray powder diffraction pattern. Additionally, due to problems such as the preferred orientation of the sample, one parameter, such as the peak height or peak area of the characteristic peak and the like, is often not the characteristic of a crystal and may not be used alone to characterize the crystal. In accordance with the general principles of crystallography, the inventors selected a series of characteristic 2θ angles and interplanar crystal spacings which can scientifically characterize the composition according to the present disclosure.

In the infrared absorption spectrum analysis, the composition according to the present disclosure has absorption peaks at the following wave numbers ±5 cm$^{-1}$: 3255, 1742, 1604, 1539, 1398, 1302, 1198, 1124, 1032, 897, 804, 600 and 479.

Preferably, in the infrared absorption spectrum analysis, the composition according to the present disclosure further has an absorption peak at the following wave numbers ±5 cm$^{-1}$: 3441, 3116, 2938, 1500 and 1099.

In the differential scanning calorimetry analysis, the composition according to the present disclosure shows an exothermic peak at 269.6±0.5° C.

With respect to the characterization of crystals, the accuracy of the infrared absorption spectroscopy and the differential scanning calorimetry analysis may be inferior to that of the X-ray powder diffraction analysis, but both of them are commonly used means for identifying substances and thus may give reference to the characterization of the composition according to the present disclosure.

The composition according to the present disclosure may be prepared by the following method: raw materials ceftriaxone sodium and sulbactam sodium are taken and ground until the particle size is from 25 μm to 88 μm, and mixed well.

Preferably, the particle size is from 25 μm to 47 μm, from 38 μm to 62 μm or from 58 μm to 88 μm.

Preferably, in the present disclosure, the grinding may be that the ceftriaxone sodium raw material and the sulbactam sodium raw material are firstly ground respectively and then ground together; and the grinding may also be that the ceftriaxone sodium raw material and the sulbactam sodium raw material are ground together directly.

Preferably, in the present disclosure, the particle size refers to the median diameter $D_{50}$.

Preferably, in the present disclosure, the grinding is performed by a ball mill.

Preferably, in the present disclosure, the mixing is performed by a single-cone ribbon mixer.

More preferably, the rotational speed of the single-cone ribbon mixer is between 25 and 40 rpm, and the mixing time is between 10 and 25 minutes.

When preparing the composition according to the present disclosure, the inventors use a grinding method. During grinding, the physical force prompts the sufficient contact between ceftriaxone sodium and sulbactam sodium, and directly or indirectly affects the microscopic spatial structure of a substance. The inventors have found that a specific degree of grinding is very important for the product; in some cases the obtained products have low crystallinity; and the degree of grinding can be controlled at a certain extent by specifying the particle size of the ground product. For example, screens with different mesh numbers may be used during grinding, and screens with specific mesh numbers may also be used to sieve the product after grinding. The particle size of the product may be determined by conventional methods in the art.

Although a preparation method of the composition according to the present disclosure is illustrated by way of example, it is not intended to rule out that there are other methods by which the composition according to the present disclosure can be obtained.

Additionally, in order to simplify the drug production process to make the subsequent preparation of pharmaceutical formulations more conveniently, the two components of the composition according to the present disclosure may also be maintained at a certain ratio in advance.

Preferably, in the composition according to the present disclosure, the ratio (in mass ratio) of ceftriaxone sodium (calculated by ceftriaxone) to sulbactam sodium (calculated by sulbactam) may be from 1:1 to 8:1. In some examples according to the present disclosure, the ratio is preferably 1:1, 2:1, 3:1, 4:1, 5:1, 6:1, 7:1 or 8:1.

More preferably, in the composition according to the present disclosure, the ratio of ceftriaxone sodium (calculated by ceftriaxone) to sulbactam sodium (calculated by sulbactam) is from 1:1 to 4:1.

Although some ratios of the components are listed, it is not intended to rule out other ratio by which the composition according to the present disclosure can be obtained.

With respect to the composition, the technical features in the above-mentioned preferred technical solutions may be combined freely and all combinations fall into the protection scope of the composition according to the present disclosure.

A further technical solution according to the present disclosure is:

a pharmaceutical formulation comprising the composition according to the present disclosure.

Preferably, in the pharmaceutical formulation according to the present disclosure, the composition according to the present disclosure is an active ingredient.

Preferably, the pharmaceutical formulation according to the present disclosure further comprises a pharmaceutical acceptable excipient.

Preferably, the pharmaceutical formulation according to the present disclosure is powder for injection or injection solution, wherein more preferably, the powder for injection is sterile powder for injection or lyophilized powder for injection.

Preferably, in the pharmaceutical formulation according to the present disclosure, the ratio (in mass ratio) of ceftriaxone sodium (calculated by ceftriaxone) to sulbactam sodium (calculated by sulbactam) may be from 1:1 to 8:1. In some examples according to the present disclosure, the ratio is preferably 1:1, 2:1, 3:1, 4:1, 5:1, 6:1, 7:1 or 8:1.

More preferably, in the pharmaceutical formulation according to the present disclosure, the mass ratio of ceftriaxone sodium (calculated by ceftriaxone) to sulbactam sodium (calculated by sulbactam) is from 1:1 to 4:1.

With respect to the pharmaceutical formulation, the technical features in the above-mentioned preferred technical solutions may be combined freely and all combinations belong to the protection scope of the pharmaceutical formulation according to the present disclosure.

Another further technical solution according to the present disclosure is:

use of the composition or the pharmaceutical formulation according to the present disclosure in the preparation of antibacterial drugs.

Preferably, in the present disclosure, the "antibacterial" according to the present disclosure refers to activity against *Neisseria gonorrhoeae*, more preferably against *Neisseria gonorrhoeae* having drug-resistance.

More preferably, in the present disclosure, the drug-resistance refers to resistance to β-lactam antibacterial drugs, tetracycline antibacterial drugs, macrolide antibacterial drugs, aminoglycoside antibacterial drugs, and fluoroquinolone antibacterial drugs.

Definitions in the present disclosure:

The term "composition" refers to a combination formed by more than one substance.

The term "pharmaceutical formulation" refers to a product which is prepared according to certain dosage form requirements, complies with provisions of relevant laws and regulations, meets requirements of relevant standards, and may be directly provided to users for use; wherein, the relevant laws and regulations include, but are not limited to, Drug Administration Law, Drug Registration and Management Regulation, Criterions for the Quality Control of Drug Manufacturing and the like; the relevant standards include, but not limited to, Chinese Pharmacopoeia.

"Sterile powder for injection", "lyophilized powder for injection" or "injection solution", as needed, can be added with excipient or not be added with excipient, and can be prepared by using conventional methods in the prior art.

"X-ray powder diffraction analysis", "infrared absorption spectrum analysis" and "differential scanning calorimetry analysis" are conventional analytical methods in the art. In addition, due to differences in experimental conditions (including, but not limited to, particle size of samples, particle aspect ratio of samples, instrument types, instrument accuracy, modes of operation, operators, etc.) and the inevitable experimental error (instrumental error, accidental error, etc.), it is impossible for the data in the present disclosure to be completely absolute values. In order to scientifically characterize the composition according to the present disclosure, the inventors specify the error range of the data depending on common knowledge in the art (for example, United States Pharmacopoeia USP35-NF30 describes that in the X-ray powder diffraction analysis, the instrumental error may reach 0.2°) and the situation of the composition according to the present disclosure. However, it will be understood that it is impossible for the error range to cover all of the situations. It will also be understood for a person skilled in the art that the numerical value may fluctuate within a range well-known in the art, which all belong to the protection scope of the technical solutions of the present disclosure.

The "peak" in "characteristic peak", "absorption peak" or "exothermic peak" refers to a peak showing greater intensity than that of noise in the spectrum pattern obtained by relevant analytical methods.

"Drug-resistant" or "drug-resistance" means that a microorganism develops resistance to a drug, so that the activity of the drug against the microorganism is reduced significantly.

A novel composition of ceftriaxone sodium and sulbactam sodium is obtained in the present disclosure through studies, and the composition and pharmaceutical formulation prepared from the same have better antibacterial activity and superior stability (physical stability, chemical stability and bioactivity stability).

In particular, after 30 months of storage, the aqueous solutions of the composition and the formulation thereof according to the present disclosure have good clarity, less than 0.5% of each of impurities, and essentially unchanged crystallinity, thereby exhibiting excellent physical and chemical stability. Furthermore, surprisingly, the composition and the pharmaceutical formulation according to the present disclosure have improved antibacterial activity, especially exhibit better antibacterial effect against a variety of drug-resistant *Neisseria gonorrhoeae*, have unchanged activity after 30 months of storage, and show superior bioactivity stability.

Due to excellent stability and bioactivity, the composition and the formulation thereof according to the present disclosure are quite suitable for the treatment of bacterial infections, especially suitable for the treatment of urogenital system infections caused by a variety of refractory and drug-resistant *Neisseria gonorrhoeae*.

DETAILED DESCRIPTION

Hereinafter, Comparative Examples, Examples and Test Examples are used to further explain the present disclosure, but are not intended to limit the technical solutions and the technical effects of the present disclosure.

Explanations for the following Comparative Examples, Examples and Test Examples:

(1) The amount of ceftriaxone sodium/ceftriaxone sodium crystals is calculated by ceftriaxone; the amount of sulbactam sodium/sulbactam sodium crystals is calculated by sulbactam, for example, "take 500 g ceftriaxone sodium" means that the amount of ceftriaxone in the taken ceftriaxone sodium is 500 g.

(2) The crystal morphology is measured by X-ray powder diffraction method using BRUKER D8 ADVANCE X-ray powder diffraction instrument under the following measurement conditions: CuKα radiation, tube voltage of 40 kV, scanning range of from 5° to 60°, scanning speed of 17.7 s/step, step-length of 0.02°.

(3) In the infrared absorption spectrum analysis, the samples are pressed into tablets with KBr and then measured;

(4) STA409 integrated thermal analyzer is purchased from a Germany company NETZSCH and is used in the differential scanning calorimetry method to perform measurement. Measurement conditions: heating rate of 10 K/min, flow rate of protective gas $N_2$ of 30 mL/min, flow rate of purging gas $N_2$ of 20 mL/min, temperature of from 35 to 300° C.

(5) The crystallinity is measured using the US Pharmacopoeia USP35-NF30 method.

(6) The content of impurity is measured using HPLC method according to the European Pharmacopoeia EP8.0 method.

(7) The clarity of solutions is measured according to the method described in Chinese Pharmacopoeia 2015.

Comparative Example 1

Figure 1:
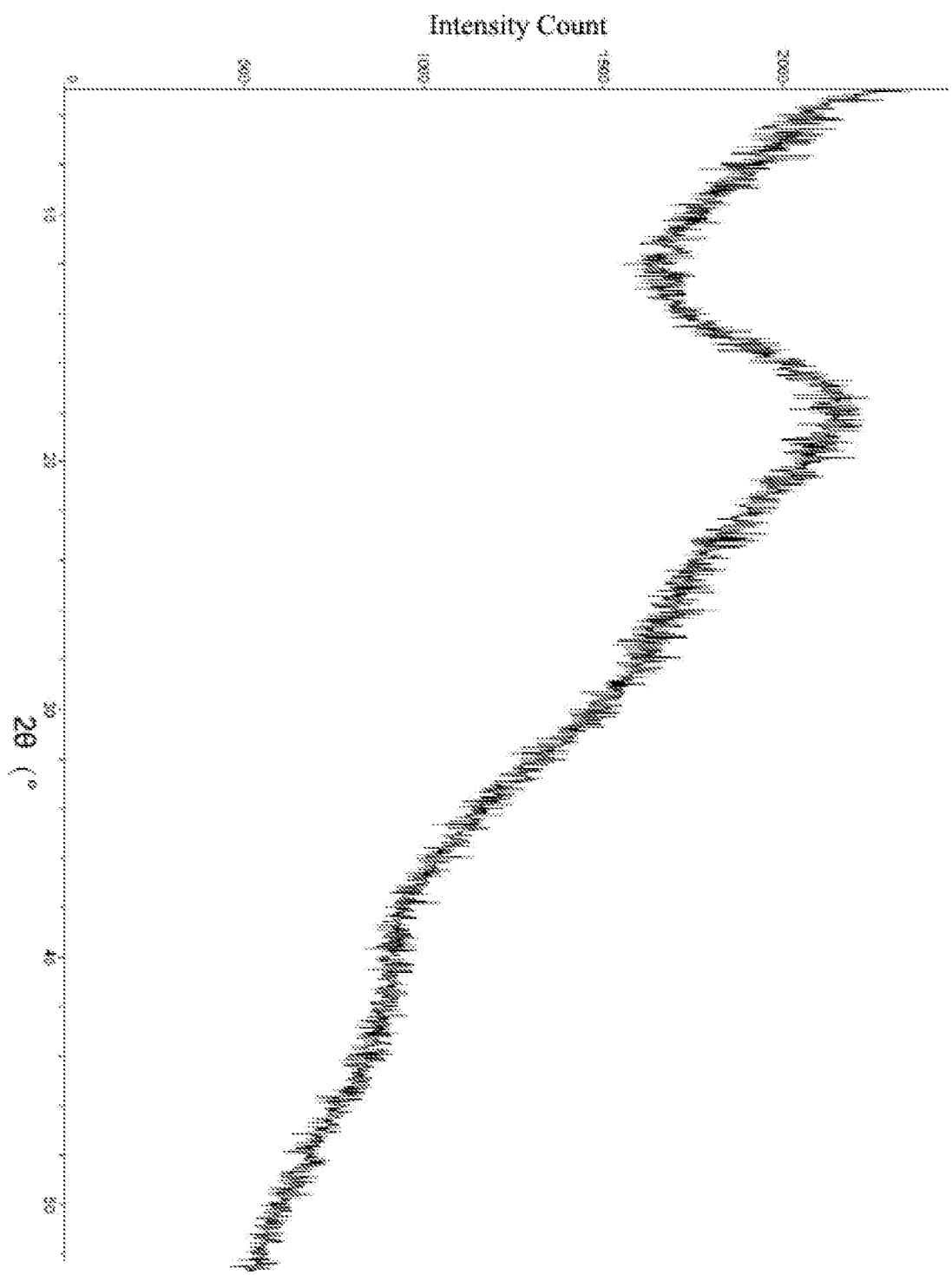
FIG. 1 shows the X-ray powder diffraction analysis spectrum for Lyophilized Powder for Injection A in Comparative Example 1.

A lyophilized powder was prepared according to the following process. In a sterile, dark condition and under nitrogen stream, 100 g of ceftriaxone sodium, 50 g of sulbactam sodium and 25 g of mannitol were added into 90 ml of pretreated 70% ethanol solution which was cooled to below 10° C. and was placed in a non-metallic container, then dissolved completely with stirring. The obtained solution was adjusted to a pH of 6.5 with 0.1 mol/L aqueous solution of sodium bicarbonate, sterile-filtered, subpackaged, placed in a lyophilizer filled with inert gas for pre-freeze (from −48° C. to −20° C.), and then subjected to pressure reduction, sublimation and drying to give the lyophilized powder named Lyophilized Powder for Injection A. The Lyophilized Powder for Injection A was sampled and determined for crystal morphology, and the X-ray powder diffraction spectrum was showed in FIG. 1.

Comparative Example 2

Ceftriaxone sodium was prepared according to the following process: condensing 7-ACT and AE-active ester to give crude product of ceftriaxone sodium; taking 5 g of the crude product and dissolving them by adding 40 ml of water; adding 4.1 g of sodium iso-octoate into the obtained solution at 13° C.; stirring until the solution was clear; adjusting the solution to a pH of 7.0 with 10% diluted hydrochloric acid; stirring for additional 30 minutes to give a mother liquor; adding anhydrous ethanol slowly into the mother liquor under stirring, until turbidity occurred; after standing for 25 minutes, slowly adding anhydrous ethanol into the solution until a large amount of crystals were formed, in which 150 ml of anhydrous ethanol was used in total; filtering the resulted crystals; washing the filter cake to neutral with a mixed solvent of anhydrous ethanol:water=4:1; washing with anhydrous ethanol again; and drying at 35° C. under ambient pressure.

Sulbactam sodium was prepared according to the following process: taking crude sulbactam sodium; adding it into a mixed solvent of N,N-dimethylformamide and water (3:1) which was 5 times (ml/g) the amount of the crude sulbactam sodium; heating to 70° C.; stirring until the crude sulbactam sodium was completely dissolved; keeping the temperature; adjusting the solution to a pH of 5.5; and making the solution flow at a speed of 5 m/s through a direct current magnetic field of 0.5 T, the direction of which was perpendicular to the flow direction of the solution; after magnetic treatment, adding activated carbon in an amount 0.3 times (ml/g) of the mixed solvent into the solution to decolor; stirring for 30 minutes and filtering to give a clear solution; adding ethanol in an amount 5 times (ml/ml) of the mixed solvent into the clear solution; filtering to give the filter cake; washing the filter cake with distilled water 3 times; and then drying for 4 hours under reduced pressure to give sulbactam sodium.

Figure 2:
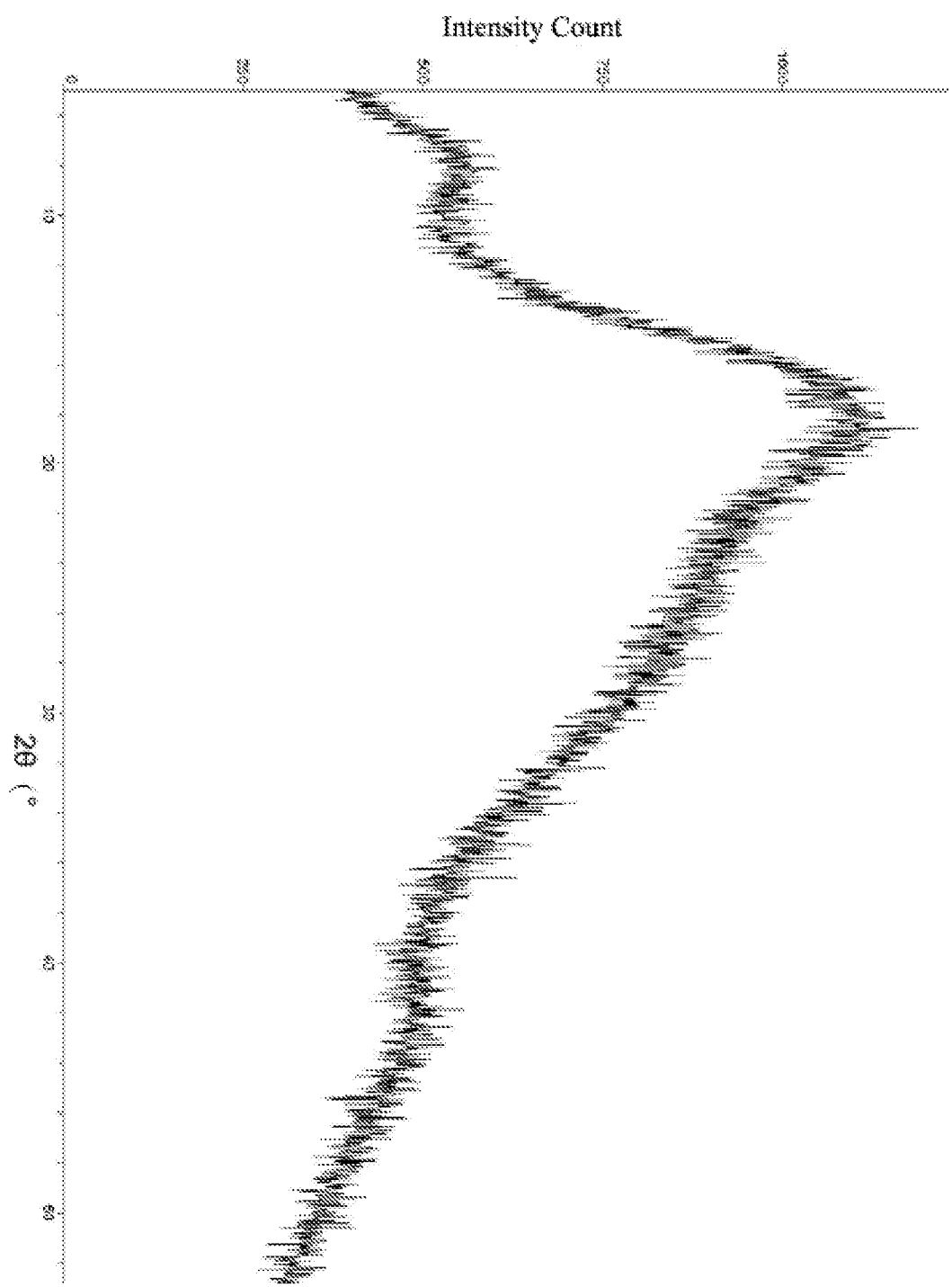
FIG. 2 shows the X-ray powder diffraction analysis spectrum for mixed powder in Comparative Example 2.

1,000 g of ceftriaxone sodium and 500 g of sulbactam sodium prepared according to the above-mentioned method were taken, mixed well by a trough mixer under sterile condition to give a mixed powder, which was sampled and subjected to crystal morphology measurement. The X-ray powder diffraction spectrum was showed in FIG. 2. The mixed powder was subpackaged under a sterile condition to give a sterile powder for injection, named sterile powder for injection A.

Comparative Example 3

2,000 g of commercially available ceftriaxone sodium and 1,000 g of commercially available sulbactam sodium were taken, mixed well through a trough mixer under sterile condition to give a mixed powder, which was sampled and measured for crystal morphology. The X-ray powder diffraction spectrum pattern of the powder was similar to that of FIG. 2. The mixed powder was subpackaged under a sterile condition to give a sterile powder for injection, named sterile powder for injection B.

Example 1

1200 g of ceftriaxone sodium and 600 g of sulbactam sodium both prepared according to the method in Comparative Example 2 were taken and ground together by a ball mill until the particle size $D_{50}$ was from 25 μm to 47 μm, and then placed in a single-cone ribbon mixer (HF1600 type) and mixed well, with rotating speed of 30 rpm and mixing for 25 minutes. After the operation was completed, the material was taken out and a crystalline substance was obtained and named Composition I.

Figure 3:
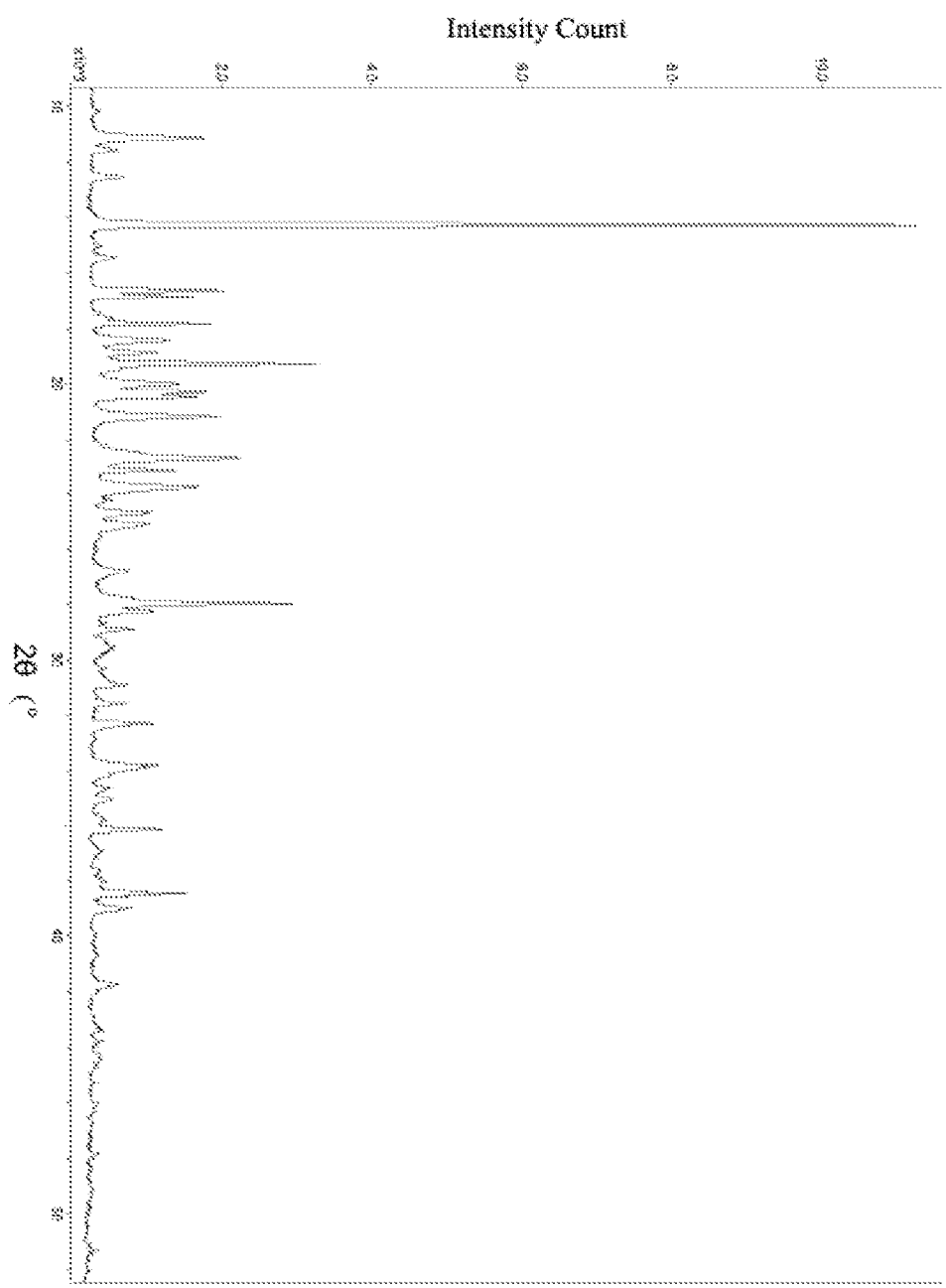
FIG. 3 shows the X-ray powder diffraction analysis spectrum for Composition I in Example 1.

The Composition I was sampled and measured for crystal morphology. The X-ray powder diffraction spectrum pattern was showed in FIG. 3. The main data of the spectrum pattern were listed in Table 1.

Figure 4:
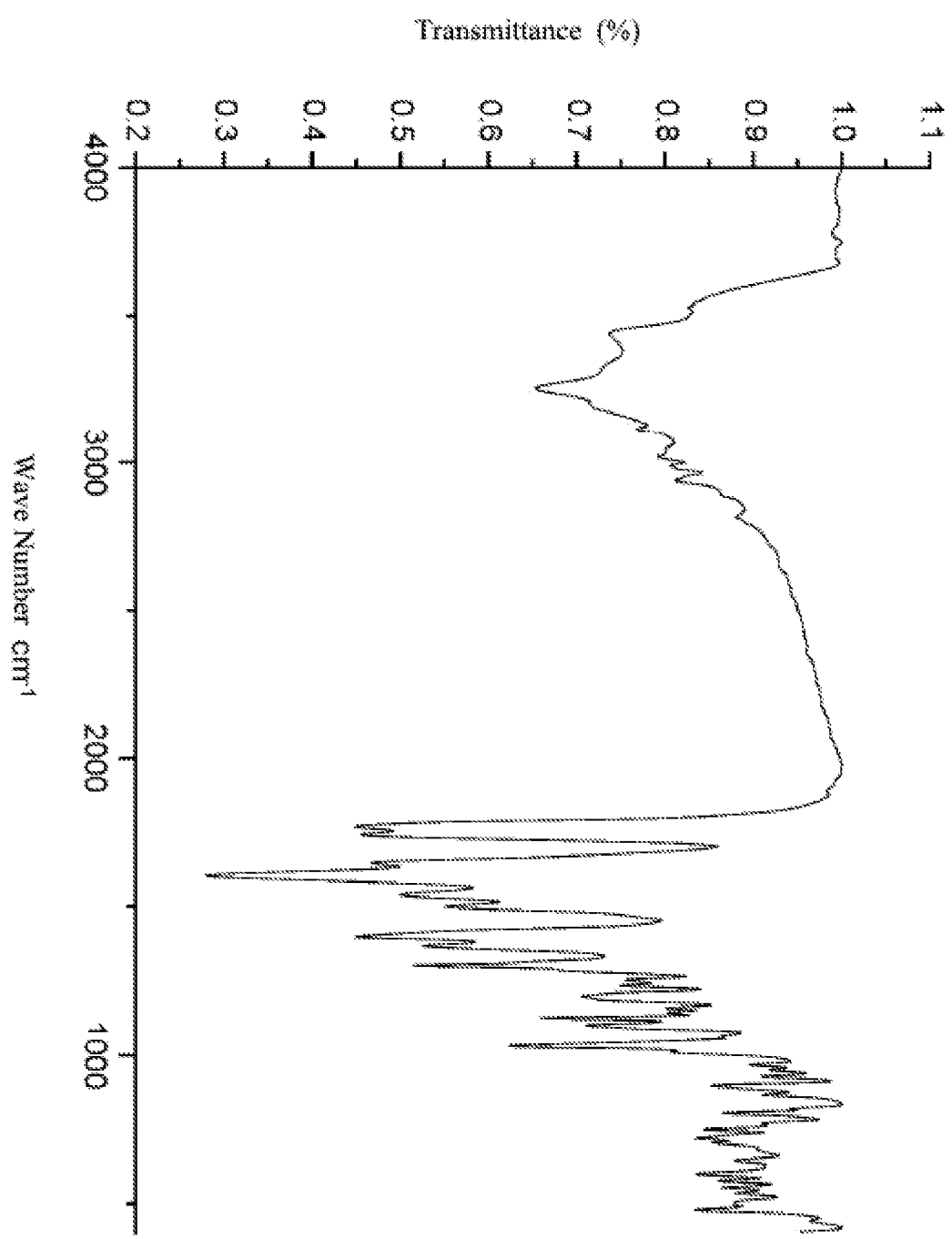
FIG. 4 shows the infrared absorption analysis spectrum for Composition I in Example 1.

Its infrared absorption was measured by infrared absorption spectrum analysis. The spectrum pattern was showed in FIG. 4. The main data of the infrared absorption peaks were listed in Table 2.

The Composition I was analyzed by the differential scanning calorimetry, and was found to have an exothermic peak at 269.51° C.

TABLE 1

Main Data of X-ray Powder Diffraction Spectrum for Composition I

| No. | 2θ Angle (°) | Interplanar Crystal Spacing(Å) | Peak Height | Peak Aera |
| --- | --- | --- | --- | --- |
| 1 | 11.138 | 7.9372 | 1502 | 16530 |
| 2 | 12.521 | 7.0634 | 437 | 4363 |

TABLE 1-continued

Main Data of X-ray Powder Diffraction Spectrum for Composition I

| No. | 2θ Angle (°) | Interplanar Crystal Spacing(Å) | Peak Height | Peak Aera |
|---|---|---|---|---|
| 3 | 14.289 | 6.1934 | 11014 | 68918 |
| 4 | 16.638 | 5.3238 | 1798 | 12883 |
| 5 | 17.835 | 4.9692 | 1569 | 11493 |
| 6 | 18.432 | 4.8096 | 883 | 7497 |
| 7 | 19.276 | 4.6008 | 2908 | 21910 |
| 8 | 19.978 | 4.4406 | 1034 | 12897 |
| 9 | 20.453 | 4.3386 | 1342 | 20418 |
| 10 | 21.171 | 4.1930 | 1651 | 17080 |
| 11 | 22.736 | 3.9079 | 1889 | 25822 |
| 12 | 23.769 | 3.7403 | 1299 | 15065 |
| 13 | 27.985 | 3.1856 | 2612 | 25393 |

TABLE 2

Main Data of Infrared Absorption Spectrum for Composition I

| No. | Wave Number(cm$^{-1}$) |
|---|---|
| 1 | 3441 |
| 2 | 3254 |
| 3 | 3117 |
| 4 | 2937 |
| 5 | 1742 |
| 6 | 1605 |
| 7 | 1539 |
| 8 | 1501 |
| 9 | 1398 |
| 10 | 1302 |
| 11 | 1198 |
| 12 | 1124 |
| 13 | 1099 |
| 14 | 1032 |
| 15 | 897 |
| 16 | 804 |
| 17 | 600 |
| 18 | 480 |

TABLE 3

Main Data of X-ray Powder Diffraction for Composition II

| No. | 2θ Angle(°) | Interplanar Crystal Spacing(Å) | Peak Height | Peak Aera |
|---|---|---|---|---|
| 1 | 11.120 | 7.9500 | 1250 | 15628 |
| 2 | 12.521 | 7.0635 | 413 | 3990 |
| 3 | 14.272 | 6.2007 | 8409 | 51004 |
| 4 | 16.656 | 5.3181 | 1282 | 10862 |
| 5 | 17.815 | 4.9746 | 1514 | 10864 |
| 6 | 18.431 | 4.8097 | 733 | 6124 |
| 7 | 19.292 | 4.5970 | 2475 | 16754 |
| 8 | 19.923 | 4.4528 | 537 | 18373 |
| 9 | 20.453 | 4.3386 | 1604 | 15208 |
| 10 | 21.171 | 4.1931 | 1308 | 13632 |
| 11 | 22.735 | 3.9080 | 1626 | 23393 |
| 12 | 23.825 | 3.7317 | 947 | 14460 |
| 13 | 27.966 | 3.1878 | 2090 | 21313 |

TABLE 4

Main Data of Infrared Absorption Spectrum for Composition II

| No. | Wave Number(cm$^{-1}$) |
|---|---|
| 1 | 3441 |
| 2 | 3254 |
| 3 | 3115 |
| 4 | 2939 |
| 5 | 1742 |
| 6 | 1605 |
| 7 | 1539 |
| 8 | 1499 |
| 9 | 1398 |
| 10 | 1302 |
| 11 | 1198 |
| 12 | 1124 |
| 13 | 1099 |
| 14 | 1032 |
| 15 | 897 |
| 16 | 804 |
| 17 | 600 |
| 18 | 478 |

Example 2

Commercially available ceftriaxone sodium 500 g and sulbactam sodium 500 g were taken, and ground together by a ball mill until the particle size D$_{50}$ was from 38 μm to 62 μm, then placed in a single-cone ribbon mixer (HF1600 type) and mixed well, with rotating speed of 40 rpm and mixing for 20 minutes. After the operation was completed, the material was taken out, and a crystalline substance was obtained and named Composition II.

Figure 5:
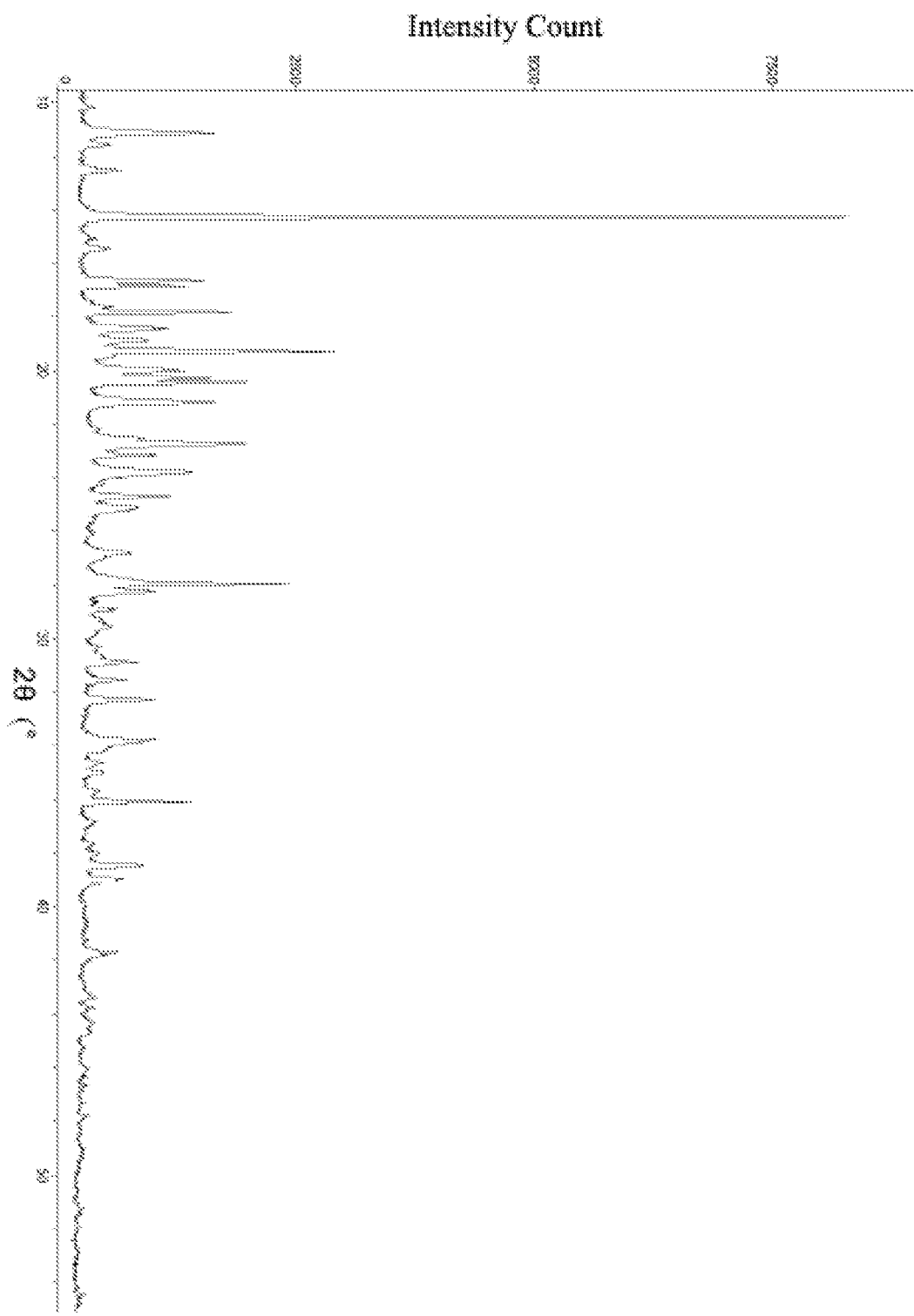
FIG. 5 shows the X-ray powder diffraction analysis spectrum for Composition II in Example 2.

The Composition II was sampled and measured for crystal morphology. The X-ray powder diffraction spectrum was showed in FIG. 5. The main data of the spectrum pattern were listed in Table 3.

Figure 6:
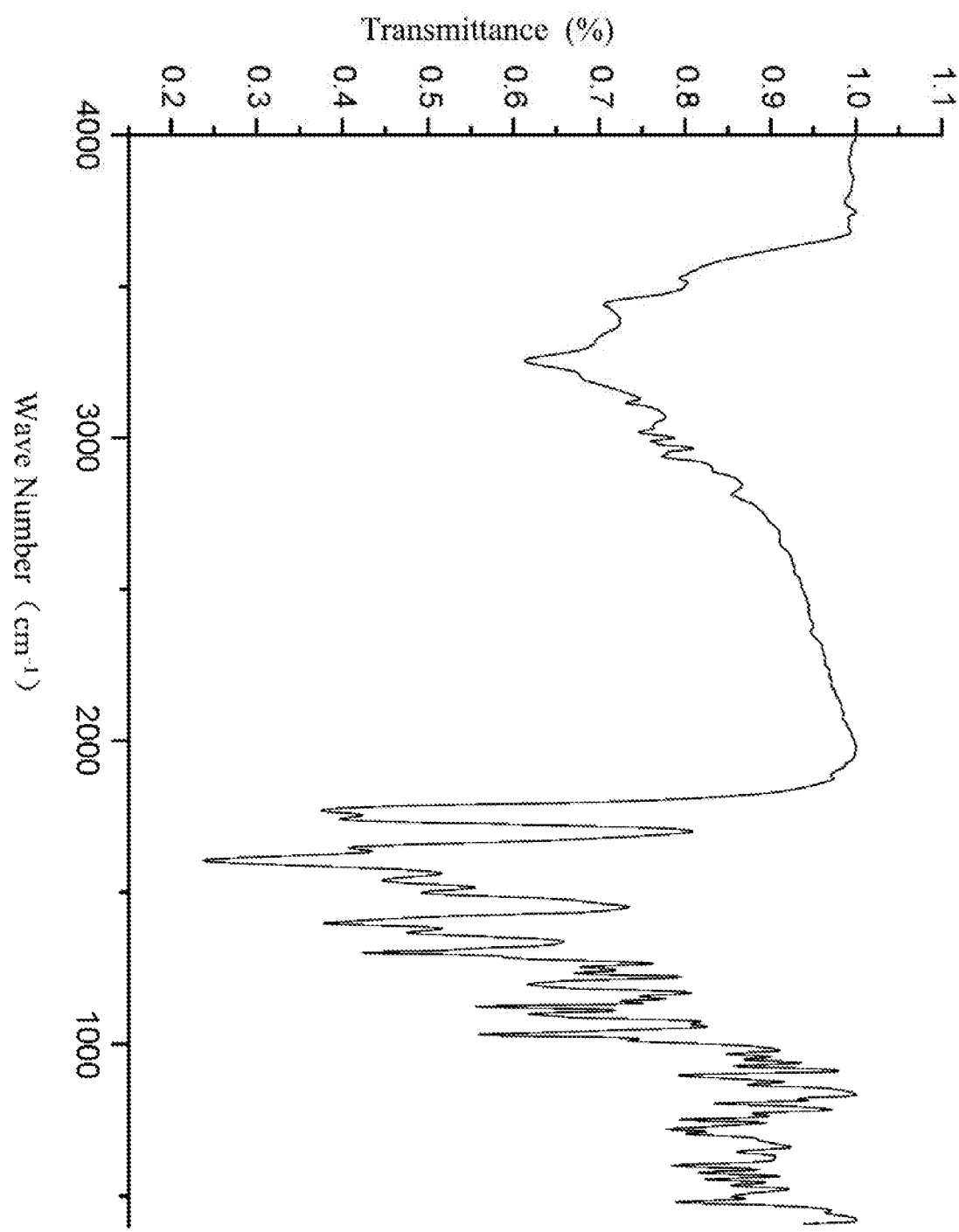
FIG. 6 shows the infrared absorption analysis spectrum for Composition II in Example 2.

Its infrared absorption was measured by infrared absorption spectrum analysis. The spectrum pattern was showed in FIG. 6. The main data of infrared absorption peaks were listed in Table 4.

The Composition II was analyzed by differential scanning calorimetry analysis, and it was found to have an exothermic peak at 269.67° C.

Example 3

930 g of commercially available ceftriaxone sodium was taken and ground; 310 g of commercially available sulbactam sodium was taken and ground; and then these two raw materials were ground together by a ball mill until the particle size D$_{50}$ was from 58 μm to 88 μm. The obtained powder was placed in a single-cone ribbon mixer (HF1600 type) and mixed well, with rotating speed of 25 rpm and mixing for 10 minutes. After the operation was completed, the material was taken out, and a crystalline substance was obtained and named Composition III.

Figure 7:
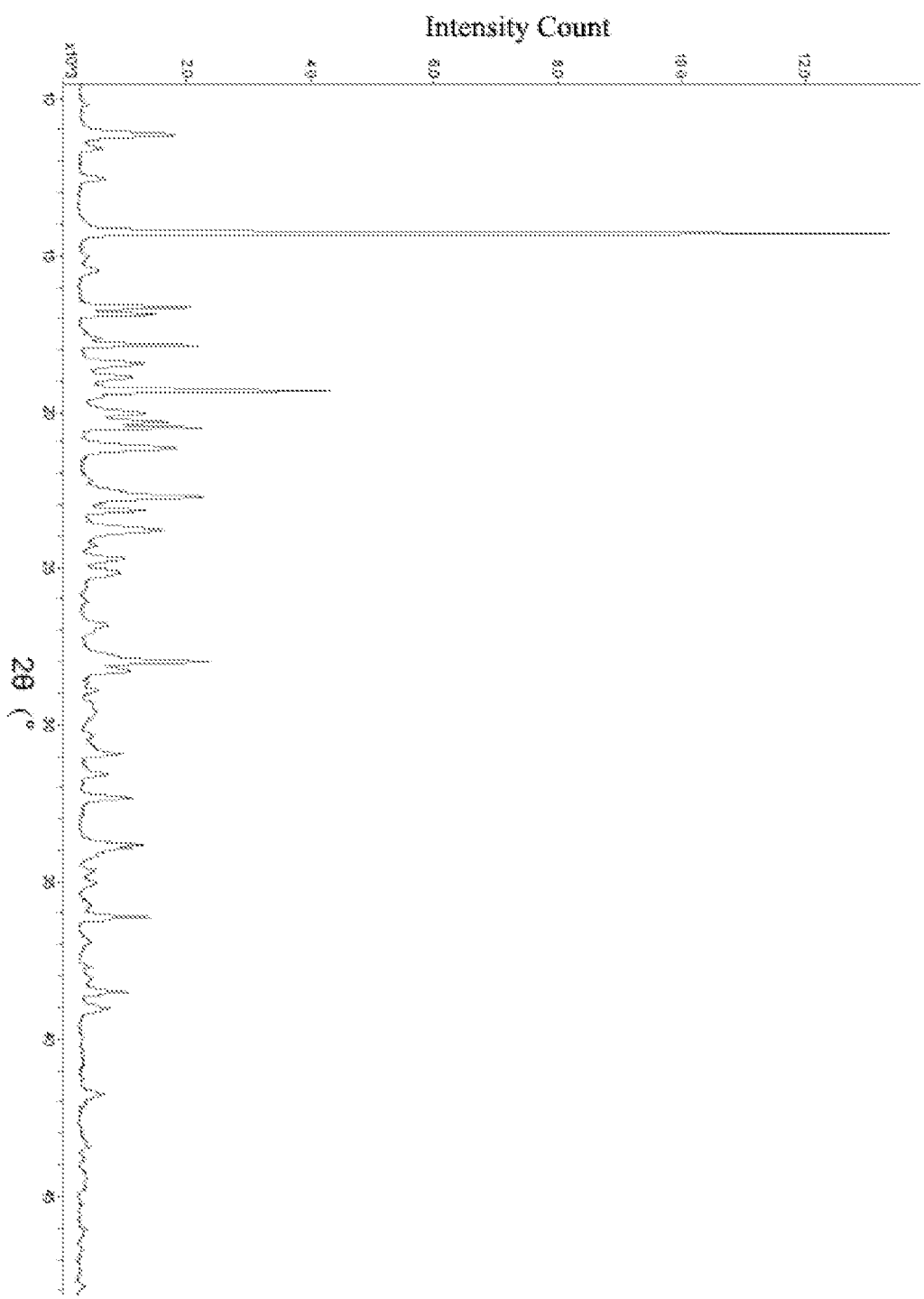
FIG. 7 shows the X-ray powder diffraction analysis spectrum for Composition III in Example 3.

The Composition III was sampled and measured for crystal morphology. The X-ray powder diffraction spectrum pattern was showed in FIG. 7. The main data of the spectrum pattern were listed in Table 5.

Figure 8:
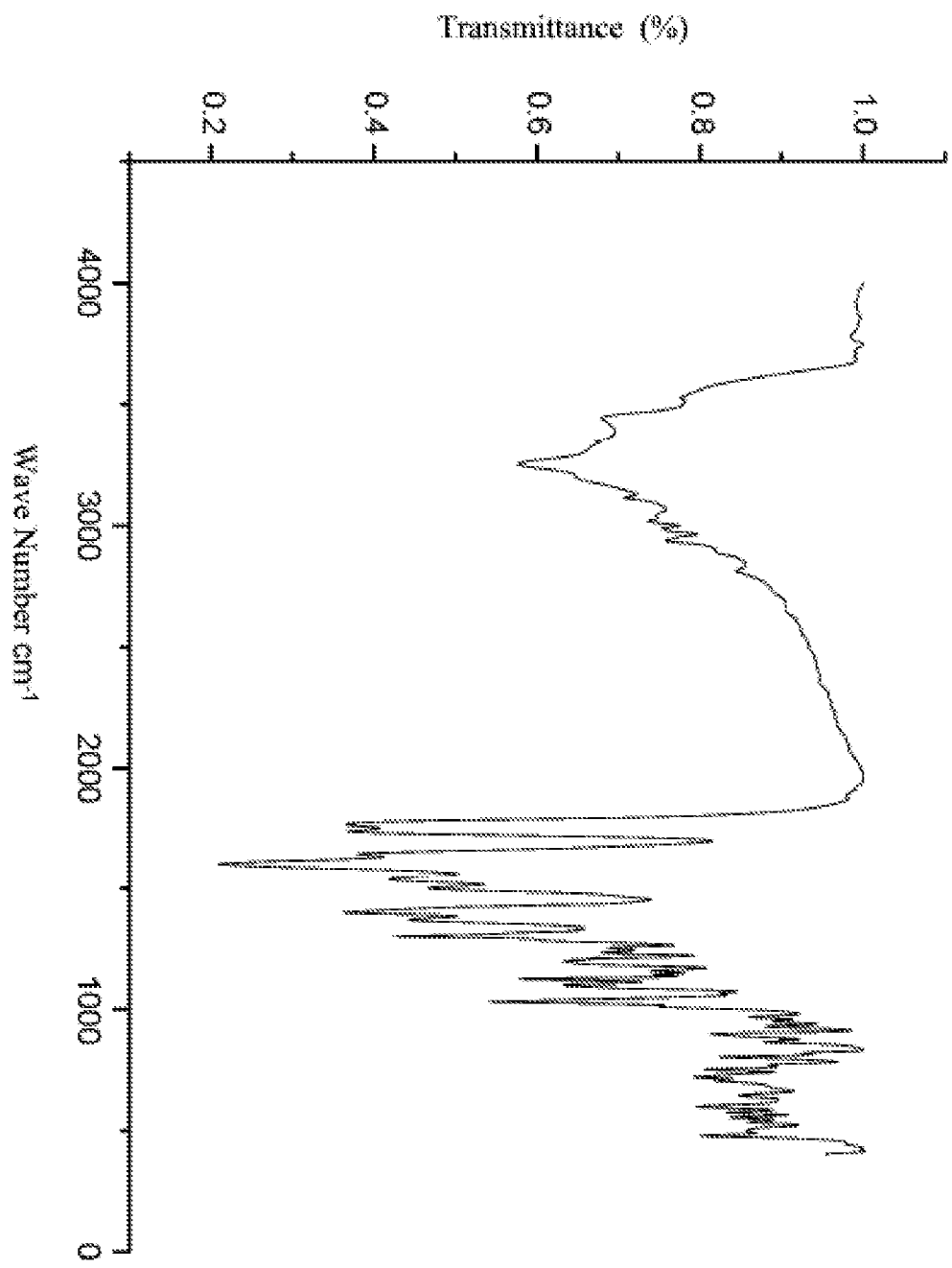
FIG. 8 shows the infrared absorption analysis spectrum for Composition III in Example 3.

Its infrared absorption was measured by infrared absorption spectrum analysis. The spectrum pattern was showed in FIG. 8. The main data of infrared absorption peaks were listed in Table 6.

The Composition III was analyzed by differential scanning calorimetry, and it was found to have an exothermic peak at 269.69° C.

TABLE 5

Main Data of X-ray Powder Diffraction for Composition III

| No. | 2θ Angle(°) | interplanar crystal spacing(Å) | Peak Height | Peak Aera |
|---|---|---|---|---|
| 1 | 11.159 | 7.9227 | 1519 | 16847 |
| 2 | 12.576 | 7.0326 | 458 | 4586 |
| 3 | 14.294 | 6.1913 | 13132 | 70185 |
| 4 | 16.658 | 5.3176 | 1786 | 11679 |
| 5 | 17.851 | 4.9647 | 1873 | 10087 |
| 6 | 18.450 | 4.8049 | 910 | 7192 |
| 7 | 19.315 | 4.5917 | 3940 | 24924 |
| 8 | 19.998 | 4.4362 | 859 | 11627 |
| 9 | 20.476 | 4.3338 | 1901 | 13788 |
| 10 | 21.208 | 4.1858 | 1446 | 16328 |
| 11 | 22.701 | 3.9138 | 1468 | 21912 |
| 12 | 23.807 | 3.7345 | 1261 | 15779 |
| 13 | 27.973 | 3.1870 | 1935 | 23623 |

TABLE 6

Main Data of Infrared Absorption Spectrum for Composition III

| No. | Wave Number(cm$^{-1}$) |
|---|---|
| 1 | 3441 |
| 2 | 3256 |
| 3 | 3117 |
| 4 | 2937 |
| 5 | 1742 |
| 6 | 1603 |
| 7 | 1539 |
| 8 | 1499 |
| 9 | 1398 |
| 10 | 1302 |
| 11 | 1198 |
| 12 | 1124 |
| 13 | 1099 |
| 14 | 1032 |
| 15 | 897 |
| 16 | 804 |
| 17 | 600 |
| 18 | 480 |

Examples 4 to 8

800 g of ceftriaxone sodium and 200 g of sulbactam sodium, 1,150 g of ceftriaxone sodium and 230 g of sulbactam sodium, 2,700 g of ceftriaxone sodium and 450 g of sulbactam sodium, 1,330 g of ceftriaxone sodium and 190 g of sulbactam sodium, 2,200 g of ceftriaxone sodium and 275 g of sulbactam sodium, all of which were commercially available, were taken respectively and then processed respectively according to the method in Example 2 to get Compositions IV to VIII respectively. It was found that the spectrum patterns of these five compositions were basically the same as those obtained in Examples 1 to 3 through X-ray diffraction analysis.

Example 9

500 g of ceftriaxone sodium and 500 g of sulbactam sodium, both of which were commercially available, were taken and ground together by a ball mill until the particle size $D_{50}$ was from 104 μm to 175 μm. The materials were mixed according to the same process as that of Example 2. After the operations were completed, the material was taken out and subpackaged under a sterile condition to give Sterile Powder for Injection C.

500 g of ceftriaxone sodium and 500 g of sulbactam sodium, both of which were commercially available, were taken again and ground together by a ball mill until the particle size $D_{50}$ was below 10 μm. The materials were mixed according to the same process as that of Example 2. After the operations were completed, the material was taken out and subpackaged under a sterile condition to give Sterile Powder for Injection D.

Example 10

The compositions of Examples 1 to 8 were taken respectively, and subpackaged under sterile condition to give Sterile Powder for Injections I to VIII.

The compositions of Examples 1 to 8 were taken respectively and processed according to the conventional process of lyophilized agents to give Lyophilized Powder for Injections I to VIII.

The compositions of Examples 1 to 8 were taken respectively and dissolved with 50 times amount of 0.9% sodium chloride aqueous solution and subpackaged to give Injections I to VIII.

Test Example 1: Stability Test

Stability test was performed for Compositions I to VIII, Sterile Powder for Injection I, Sterile Powder for Injection II, Sterile Powder for Injection IV, Lyophilized Powder for Injection I, Lyophilized Powder for Injection II, Sterile Powder for Injection A, Sterile Powder for Injection B, Sterile Powder for Injection C, Sterile Powder for Injection D and Lyophilized Powder for Injection A obtained in the above-mentioned Comparative Examples or Examples.

Test environment: placing under 25° C.±2° C. and 60%±10% relative humidity condition for 30 months.

Test results: clarity of solution; contents of impurities 1, 2, 3 and 4 (wherein, impurities 1, 2 and 3 were respectively impurities A, B and E of ceftriaxone sodium described in EP8.0, and impurity 4 was impurity A of sulbactam sodium described in EP8.0), crystallinity and the like were measured and main test results were shown in Tables 7 to 10.

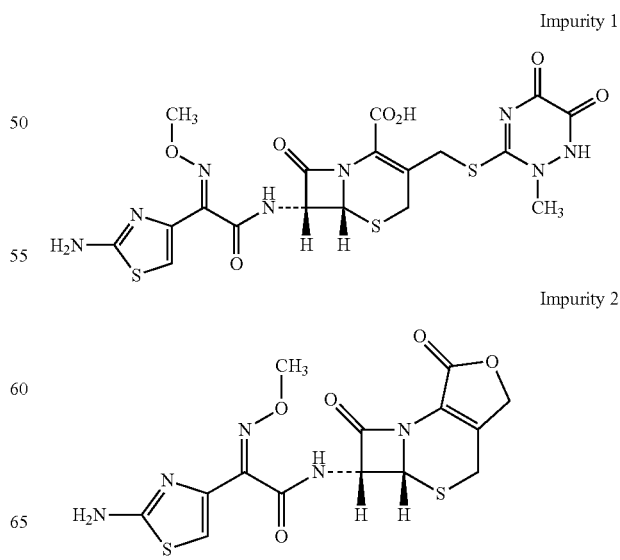

Impurity 1

Impurity 2

Impurity 3

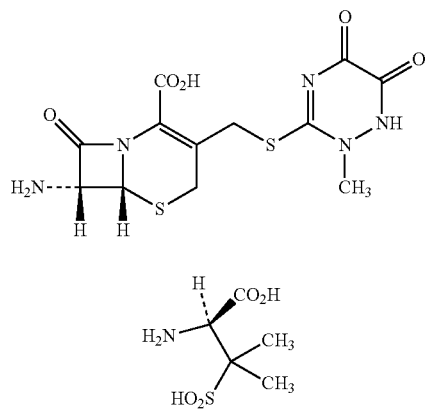

Impurity 4

TABLE 7

Situations of Various Samples at $0^{th}$ Month in Stability Test

| Samples | Crys-tallinity (%) | Content of Impurity 1 (%) | Content of Impurity 2 (%) | Content of Impurity 3 (%) | Content of Impurity 4 (%) | Clarity of Solution |
|---|---|---|---|---|---|---|
| Composition I | 90.5 | 0.12 | 0.08 | 0.09 | 0.11 | Clear |
| Composition II | 92.7 | 0.15 | 0.10 | 0.13 | 0.12 | Clear |
| Composition III | 91.2 | 0.12 | 0.14 | 0.15 | 0.14 | Clear |
| Composition IV | 92.1 | 0.11 | 0.20 | 0.12 | 0.10 | Clear |
| Composition V | 90.4 | 0.18 | 0.27 | 0.19 | 0.10 | Clear |
| Composition VI | 91.7 | 0.09 | 0.15 | 0.16 | 0.18 | Clear |
| Composition VII | 92.5 | 0.21 | 0.10 | 0.15 | 0.13 | Clear |
| Composition VIII | 92.1 | 0.29 | 0.27 | 0.18 | 0.22 | Clear |
| Sterile Powder for Injection I | 90.6 | 0.14 | 0.10 | 0.15 | 0.15 | Clear |
| Sterile Powder for Injection II | 92.3 | 0.14 | 0.11 | 0.14 | 0.14 | Clear |
| Sterile Powder for Injection IV | 90.4 | 0.17 | 0.16 | 0.15 | 0.12 | Clear |
| Lyophilized Powder for Injection I | 87.6 | 0.12 | 0.20 | 0.16 | 0.17 | Clear |
| Lyophilized Powder for Injection II | 85.3 | 0.16 | 0.20 | 0.21 | 0.18 | Clear |
| Lyophilized Powder for Injection A | / | 0.32 | 0.14 | 0.22 | 0.11 | Clear |
| Sterile Powder for Injection A | / | 0.18 | 0.13 | 0.26 | 0.18 | Clear |
| Sterile Powder for Injection B | / | 0.33 | 0.19 | 0.18 | 0.19 | Clear |
| Sterile Powder for Injection C | 78.2 | 0.25 | 0.21 | 0.20 | 0.18 | Clear |
| Sterile Powder for Injection D | 72.1 | 0.22 | 0.31 | 0.23 | 0.16 | Clear |

TABLE 8

Situations of Various Samples at $12^{th}$ Month in Stability Test

| Samples | Crys-tallinity (%) | Content of Impurity A (%) | Content of Impurity B (%) | Content of Impurity E (%) | Content of Impurity G (%) | Clarity of Solution |
|---|---|---|---|---|---|---|
| Composition I | 90.4 | 0.14 | 0.10 | 0.11 | 0.14 | Clear |
| Composition II | 91.6 | 0.18 | 0.11 | 0.15 | 0.14 | Clear |
| Composition III | 91.3 | 0.19 | 0.16 | 0.17 | 0.17 | Clear |
| Composition IV | 92.0 | 0.21 | 0.25 | 0.17 | 0.14 | Clear |
| Composition V | 89.2 | 0.16 | 0.30 | 0.24 | 0.13 | Clear |
| Composition VI | 91.1 | 0.15 | 0.21 | 0.18 | 0.22 | Clear |
| Composition VII | 92.4 | 0.26 | 0.24 | 0.21 | 0.14 | Clear |
| Composition VIII | 91.9 | 0.31 | 0.29 | 0.19 | 0.22 | Clear |
| Sterile Powder for Injection I | 90.8 | 0.25 | 0.14 | 0.23 | 0.18 | Clear |
| Sterile Powder for Injection II | 92.7 | 0.19 | 0.17 | 0.24 | 0.15 | Clear |
| Sterile Powder for Injection IV | 91.7 | 0.22 | 0.19 | 0.20 | 0.15 | Clear |
| Lyophilized Powder for Injection I | 85.8 | 0.16 | 0.23 | 0.19 | 0.18 | Clear |
| Lyophilized Powder for Injection II | 85.7 | 0.22 | 0.21 | 0.26 | 0.19 | Clear |
| Lyophilized Powder for Injection A | / | 0.53 | 0.38 | 0.46 | 0.54 | Clear |
| Sterile Powder for Injection A | / | 0.69 | 0.52 | 0.32 | 0.41 | Clear |
| Sterile Powder for Injection B | / | 0.53 | 0.48 | 0.37 | 0.43 | Clear |
| Sterile Powder for Injection C | 75.1 | 0.34 | 0.31 | 0.29 | 0.34 | Clear |
| Sterile Powder for Injection D | 73.2 | 0.29 | 0.42 | 0.33 | 0.30 | Clear |

TABLE 9

Situations of Various Samples at $24^{th}$ Month in Stability Test

| Samples | Crys-tallinity (%) | Content of Impurity A (%) | Content of Impurity B (%) | Content of Impurity E (%) | Content of Impurity G (%) | Clarity of Solution |
|---|---|---|---|---|---|---|
| Composition I | 89.2 | 0.18 | 0.21 | 0.17 | 0.25 | Clear |
| Composition II | 91.0 | 0.20 | 0.10 | 0.19 | 0.23 | Clear |
| Composition III | 90.4 | 0.23 | 0.20 | 0.21 | 0.26 | Clear |
| Composition IV | 91.7 | 0.21 | 0.29 | 0.23 | 0.17 | Clear |
| Composition V | 88.2 | 0.28 | 0.33 | 0.29 | 0.30 | Clear |
| Composition VI | 91.0 | 0.19 | 0.27 | 0.28 | 0.23 | Clear |
| Composition VII | 91.6 | 0.33 | 0.27 | 0.32 | 0.22 | Clear |
| Composition VIII | 91.7 | 0.35 | 0.35 | 0.23 | 0.29 | Clear |
| Sterile Powder for Injection I | 90.1 | 0.34 | 0.26 | 0.37 | 0.26 | Clear |
| Sterile Powder for Injection II | 91.9 | 0.21 | 0.20 | 0.35 | 0.22 | Clear |
| Sterile Powder for Injection IV | 91.4 | 0.23 | 0.38 | 0.24 | 0.22 | Clear |
| Lyophilized Powder for Injection I | 85.2 | 0.23 | 0.29 | 0.33 | 0.22 | Clear |
| Lyophilized Powder for Injection II | 84.1 | 0.30 | 0.32 | 0.29 | 0.30 | Clear |

TABLE 9-continued

Situations of Various Samples at 24th Month in Stability Test

| Samples | Crys-tallinity (%) | Content of Impurity A (%) | Content of Impurity B (%) | Content of Impurity E (%) | Content of Impurity G (%) | Clarity of Solution |
|---|---|---|---|---|---|---|
| Lyophilized Powder for Injection A | / | 0.83 | 0.77 | 0.88 | 0.62 | Clear |
| Sterile Powder for Injection A | / | 0.99 | 0.82 | 0.79 | 0.70 | Slightly turbid |
| Sterile Powder for Injection B | / | 0.78 | 0.97 | 0.85 | 0.75 | Slightly turbid |
| Sterile Powder for Injection C | 64.0 | 0.38 | 0.47 | 0.59 | 0.41 | Clear |
| Sterile Powder for Injection D | 62.2 | 0.39 | 0.56 | 0.44 | 0.33 | Clear |

TABLE 10

Situations of Various Samples at 30th Month in Stability Test

| Samples | Crys-tallinity (%) | Content of Impurity A (%) | Content of Impurity B (%) | Content of Impurity E (%) | Content of Impurity G (%) | Clarity of Solution |
|---|---|---|---|---|---|---|
| Composition I | 88.1 | 0.32 | 0.31 | 0.33 | 0.31 | Clear |
| Composition II | 90.5 | 0.31 | 0.29 | 0.34 | 0.30 | Clear |
| Composition III | 88.2 | 0.38 | 0.37 | 0.28 | 0.34 | Clear |
| Composition IV | 90.0 | 0.43 | 0.32 | 0.32 | 0.31 | Clear |
| Composition V | 87.1 | 0.37 | 0.45 | 0.32 | 0.33 | Clear |
| Composition VI | 89.9 | 0.25 | 0.33 | 0.33 | 0.30 | Clear |
| Composition VII | 90.5 | 0.38 | 0.41 | 0.39 | 0.33 | Clear |
| Composition VIII | 90.2 | 0.45 | 0.41 | 0.31 | 0.31 | Clear |
| Sterile Powder for Injection I | 88.5 | 0.47 | 0.45 | 0.42 | 0.38 | Clear |
| Sterile Powder for Injection II | 89.7 | 0.37 | 0.39 | 0.39 | 0.33 | Clear |
| Sterile Powder for Injection IV | 90.2 | 0.43 | 0.42 | 0.37 | 0.36 | Clear |
| Lyophilized Powder for Injection I | 84.9 | 0.39 | 0.39 | 0.43 | 0.38 | Clear |
| Lyophilized Powder for Injection II | 83.7 | 0.47 | 0.38 | 0.42 | 0.31 | Clear |
| Lyophilized Powder for Injection A | / | 1.23 | 1.05 | 1.12 | 0.78 | Slightly turbid |
| Sterile Powder for Injection A | / | 1.36 | 1.12 | 0.94 | 1.19 | Slightly turbid |
| Sterile Powder for Injection B | / | 1.13 | 0.99 | 1.27 | 1.06 | Slightly turbid |
| Sterile Powder for Injection C | 60.6 | 0.57 | 0.62 | 0.70 | 0.47 | Clear |
| Sterile Powder for Injection D | 53.5 | 0.65 | 0.71 | 0.58 | 0.42 | Clear |

It can be seen from the results of the stability test that after 12 months, the compositions and the formulations according to the present disclosure, as compared with Comparative Examples, had differences in the following aspects such as crystallinity, impurities, clarity of solution and the like; and after 30 months, such differences were more significant.

The formulations of Comparative Examples did not show a crystalline form and there was no data of crystallinity; however, the compositions and formulations according to the present disclosure had a crystallinity of up to 90%, which kept substantially unchanged within 30 months and showed very good physical stability.

At $24^{th}$-$30^{th}$ month, the formulations of Comparative Examples showed slight turbidity, and the compositions and the formulations according to the present disclosure did not show turbidity.

Although, the contents of four impurities in the formulations of Comparative Examples were equivalent to those in the compositions according to the present disclosure at $0^{th}$ month, the increase of impurities was very significant as time passed. Especially, the contents of impurity 1 (an isomer impurity of ceftriaxone) and impurity 4 (an open-loop degraded impurity of sulbactam) ware greater than 1% and greater than 0.5% respectively at $24^{th}$-$30^{th}$ month, and failed to meet the requirements of EP 8.0. However, the contents of the four impurities in the compositions and the formulations according to the present disclosure were not significantly increased and in a defined scope, indicating very good chemical stability. This finding revealed that there may be a close relation between the generation of specific impurities and crystal morphology.

Test Example 2: In Vivo Antibacterial Test

The stability test samples in test example 1 were sampled at $0^{th}$ month and subjected to in vivo antibacterial test; and the stability test samples were sampled at 30th month again, and subjected to in vivo antibacterial test. The in vivo antibacterial tests were performed according to the following method.

2.1 Test Materials

Test Samples: Compositions I to VIII, Sterile Powder for Injection I, Sterile Powder for Injection II, Sterile Powder for Injection IV, Lyophilized Powder for Injection I, Lyophilized Powder for Injection II, Lyophilized Powder for Injection A, Sterile Powder for Injection A and Sterile Powder for Injection B, all of which were obtained from the test example 1 at $0^{th}$ and $30^{th}$ month; and control drugs: ceftriaxone sodium, levofloxacin hydrochloride, azithromycin, doxycycline hydrochloride and spectinomycin hydrochloride, wherein, a batch of the control drugs were purchased at $0^{th}$ month of the stability test so as to match with the test samples at $0^{th}$ month, and another batch of control drugs were purchased at 30th month of the stability test so as to match with the test samples at 30th month, and the time when the two batches were purchased was within one month from the date of their production.

Animals: ICR mice weighed 18-22 g, half male and half female.

Strains: ATCC700603 (*Klebsiella pneumoniae*), ATCC43069 (*Neisseria gonorrhoeae*), Q-R (quinolone-resistant *Neisseria gonorrhoeae*), T-R (tetracycline-resistant *Neisseria gonorrhoeae*), PP-R (β-lactam-resistant *Neisseria gonorrhoeae*), MAC-R (macrolide-resistant *Neisseria gonorrhoeae*), SPE-R (spectinomycin-resistant *Neisseria gonorrhoeae*) and QS-R (ceftriaxone-resistant *Neisseria gonorrhoeae*), wherein, ATCC700603, and ATCC43069 were purchased from ATCC; QS-R was prepared by in vitro inducing *Neisseria gonorrhoeae*, which was sensitive to ceftriaxone, with a subinhibitory concentration of ceftriaxone, culturing at 36° C., 5% $CO_2$, passaging once every 24 hours, and then transferring to a higher concentration of ceftriaxone on GC medium until the strain was resistant to ceftriaxone; and other strains were clinical isolates.

Protective agent: highly active dry yeast.

2.2 Test Method

Enhancing Cytotoxicity:

After incubating for 18 hours, the experimental strain was diluted to $10^{-2}$ and $10^{-3}$ with 5% highly active dry yeast; 0.5 ml of the strain was injected intraperitoneally into mice to induce systemic infection, resulting in a septicemia mouse model. No protective measures was provided and thus mice died of infection. Aseptic thoracotomy was performed timely on the mice died of infection, the heart blood or intracavity effusion was taken and evenly coated on corresponding agar plates, and incubated for 18 hours at 37° C. The strain was identified to be consistent with the administrated infectious bacteria. The obtained strain was used to infect mice again. By repeating this method 1-2 times, the cytotoxicity of the strain could be enhanced and was relatively stable.

Determining Minimum Lethal Dose (MLD):

the experimental strain was diluted with 5% highly active dry yeast to give diluted bacteria solutions at different concentrations: $10^{-1}$, $10^{-2}$, $10^{-3}$ and $10^{-4}$, which were injected intraperitoneally into experimental animals (0.5 ml per mouse) respectively to establish a septicemia model. After infection, the number of dead mice was recorded. The minimum dose causing 100% death of mice was 1 MLD, and was used as the dose in animal protection experiments. The bacterial concentration, which was one log lower than 1 MLD and infected the animals without mortality, was named 0.1 MLD. In experiments, a bacteria concentration of 1 MLD was used as the positive control for the infection experiments; and a bacteria concentration of 0.1 MLD was used as the negative control for the infection. In both positive and negative control groups, only the bacteria were administrated and no antibiotic treatment was provided. The mortality of the positive group should be 70% or more, and the mortality of the negative group should be 30% or less.

Pre-Test for Determining the Dose Range of Test Samples:

1 MLD of bacteria was formulated with 5% highly active dry yeast and used to infect mice Immediately and after 6 hours, pre-tests were performed using test samples at three different concentrations (high concentration, medium concentration and low concentration), 4 mice per dose group. The survival number of mice was recorded after infection, and based on this result, the administration dose in the animal protection test was designed. When the administration dosage was investigated first, there may be relatively great differences between the dose concentrations of the groups. When the range of the administration dosage was determined, it may be further investigated by reducing the differences until the suitable administration dosage (that is, for the group administrated with the highest concentration, 70% or more infected animals survived; and for the group administrated with the lowest concentration, no less than 70% of infected animals died) was found.

Animal Protection Test:

In the pre-tests, the drug dosages at which 100% of mice died or no death occurred were obtained for the mice infected with the test strains. Then, the mice were fasted from food other than water for 18 hours before experiment, weighted 18-22 g; half male and half female. The mice were randomly divided into the following groups: (1) ATCC700603 group, (2) ATCC43069 group, (3) Q-R group, (4) T-R group, (5) PP-R group, (6) MAC-R group, (7) SPE-R group and (8) QS-R group; with five test sample concentrations per group, and 10 animals per group. 10 animals were used as blank controls (equal volume of sterile water for injection was administrated). Each mouse was injected intraperitoneally with 0.5 ml of 1 MLD bacteria solution to establish an infection model Immediately and after 6 hours, test sample solutions at different concentrations were injected subcutaneously respectively at 0.2 ml per mouse. The mice were observed for 7 consecutive days, and the death status of animals in each group were recorded. The dead mice were investigated with autopsy and observed with naked eye. The 50% effective dose ($ED_{50}$) and 95% confidence intervals were calculated by Bliss method; t-test was performed to determine the significant difference between groups. The lower the $ED_{50}$ was, the better the protection for animals infected by bacteria the test sample provided.

2.3 Test Results

Main results of the animal protection tests were listed in Table 11 and Table 12, wherein, Table 11 showed the in vivo antibacterial $ED_{50}$ values of the samples at $0^{th}$ month of the stability test, and Table 12 showed the in vivo antibacterial $ED_{50}$ values of the samples at $30^{th}$ month of the stability test.

TABLE 11

In Vivo Antibacterial $ED_{50}$ Values of Samples at $0^{th}$ Month of the Stability Test (mg/kg)

| Test Samples | Strains | | | | | | | |
|---|---|---|---|---|---|---|---|---|
| | ATCC 700603 | ATCC 43069 | Q-R | T-R | PP-R | MAC-R | SPE-R | QS-R |
| Ceftriaxone Sodium | 35 | 16 | 31 | 46 | 208 | 34 | 52 | 337 |
| Levofloxacin Hydrochloride | — | 25 | 573 | 48 | 37 | 36 | 67 | 72 |
| Azithromycin | — | 24 | 43 | 62 | 49 | 487 | 59 | 63 |
| Doxycycline Hydrochloride | — | 37 | 55 | 456 | 52 | 58 | 52 | 105 |
| Spectinomycin Hydrochloride | — | 19 | 40 | 61 | 56 | 38 | 621 | 41 |
| Composition I | 21 | 11 | 24 | 34 | 47 | 27 | 42 | 62 |
| Composition II | 23 | 13 | 21 | 37 | 50 | 23 | 42 | 65 |
| Composition III | 19 | 14 | 22 | 35 | 45 | 25 | 46 | 59 |
| Composition IV | 22 | 15 | 20 | 32 | 44 | 26 | 47 | 62 |
| Composition V | 27 | 13 | 26 | 37 | 56 | 27 | 49 | 78 |
| Composition VI | 30 | 16 | 25 | 38 | 68 | 27 | 48 | 85 |
| Composition VII | 31 | 17 | 25 | 38 | 60 | 29 | 52 | 82 |
| Composition VIII | 28 | 15 | 27 | 39 | 66 | 28 | 50 | 84 |
| Sterile Powder for Injection I | 25 | 13 | 24 | 32 | 42 | 25 | 46 | 64 |

TABLE 11-continued

In Vivo Antibacterial ED$_{50}$ Values of Samples at 0$^{th}$ Month of the Stability Test (mg/kg)

| Test Samples | ATCC 700603 | ATCC 43069 | Q-R | T-R | PP-R | MAC-R | SPE-R | QS-R |
|---|---|---|---|---|---|---|---|---|
| Sterile Powder for Injection II | 27 | 10 | 23 | 35 | 48 | 27 | 43 | 67 |
| Sterile Powder for Injection IV | 24 | 14 | 25 | 34 | 46 | 26 | 44 | 66 |
| Lyophilized Powder for Injection I | 27 | 14 | 22 | 35 | 43 | 24 | 46 | 62 |
| Lyophilized Powder for Injection II | 28 | 12 | 23 | 37 | 41 | 22 | 45 | 60 |
| Lyophilized Powder for Injection A | 31 | 16 | 27 | 39 | 62 | 26 | 50 | 95 |
| Sterile Powder for Injection A | 32 | 15 | 30 | 40 | 56 | 29 | 48 | 92 |
| Sterile Powder for Injection B | 33 | 16 | 32 | 38 | 49 | 24 | 46 | 94 |

Note:
— represents Not Performed.

TABLE 12

In Vivo Antibacterial ED$_{50}$ Values of Samples at 30$^{th}$ Month of the Stability Test (mg/kg)

| Test Samples | ATCC 700603 | ATCC 43069 | Q-R | T-R | PP-R | MAC-R | SPE-R | QS-R |
|---|---|---|---|---|---|---|---|---|
| Ceftriaxone Sodium | 37 | 21 | 30 | 57 | 224 | 37 | 66 | 373 |
| Levofloxacin Hydrochloride | — | 30 | 564 | 43 | 42 | 41 | 72 | 82 |
| Azithromycin | — | 31 | 40 | 59 | 55 | 497 | 65 | 69 |
| Doxycycline Hydrochloride | — | 32 | 51 | 432 | 47 | 62 | 51 | 99 |
| Spectinomycin Hydrochloride | — | 22 | 42 | 68 | 67 | 42 | 571 | 56 |
| Composition I | 23 | 16 | 22 | 42 | 50 | 29 | 52 | 71 |
| Composition II | 25 | 15 | 20 | 46 | 53 | 27 | 49 | 69 |
| Composition III | 19 | 14 | 20 | 45 | 56 | 29 | 48 | 68 |
| Composition IV | 25 | 17 | 24 | 42 | 51 | 25 | 57 | 70 |
| Composition V | 31 | 20 | 27 | 48 | 68 | 31 | 55 | 87 |
| Composition VI | 37 | 20 | 28 | 51 | 75 | 28 | 59 | 88 |
| Composition VII | 38 | 22 | 28 | 47 | 65 | 33 | 57 | 92 |
| Composition VIII | 36 | 23 | 26 | 49 | 71 | 31 | 59 | 94 |
| Sterile Powder for Injection I | 26 | 16 | 21 | 41 | 51 | 28 | 48 | 75 |
| Sterile Powder for Injection II | 30 | 17 | 20 | 43 | 52 | 28 | 47 | 69 |
| Sterile Powder for Injection IV | 28 | 16 | 22 | 39 | 56 | 27 | 46 | 71 |
| Lyophilized Powder for Injection I | 30 | 18 | 26 | 42 | 53 | 25 | 47 | 70 |
| Lyophilized Powder for Injection II | 29 | 17 | 24 | 48 | 61 | 25 | 48 | 67 |
| Lyophilized Powder for Injection A | 35 | 26 | 41 | 78 | 93 | 53 | 79 | 153 |
| Sterile Powder for Injection A | 36 | 28 | 47 | 75 | 102 | 48 | 87 | 174 |
| Sterile Powder for Injection B | 35 | 28 | 46 | 77 | 106 | 47 | 91 | 188 |

Note:
"—" represents Not Performed.

The test results showed that the compositions and the formulations according to the present disclosure had better antibacterial activity, and especially exhibited significantly higher inhibitory activity against various drug-resistant *Neisseria gonorrhoeae* bacteria and in some cases the activity may increase 3-4 times as compared with the formulations in Comparative Examples.

In addition, the compositions and the formulations according to the present disclosure had relatively good stability of biological activity, and particularly had stable inhibitory activity against various non-drug-resistant and drug-resistant *Neisseria gonorrhoeae*. The compositions and the formulations according to the present disclosure had basically unchanged biological activity after 30 months. In contrast, the formulations in the comparative examples showed significant reduction in the activity after 30 months.

Although the present disclosure has been described above in detail with general description, specific embodiments and tests, a person skilled in the art may make suitable modifications or improvements thereon based on the present disclosure. Thus, those modifications or improvements made without departing from the spirits of the present disclosure all belong to the content of the present disclosure. The background, summary of the disclosure, and specific modes for carrying out the present disclosure are only for illustrative purpose, but not used as evidence for identifying the prior art of the present disclosure.

What is claimed is:

1. A crystalline composition consisting essentially of ceftriaxone sodium and sulbactam sodium and having an X-ray powder diffraction pattern with peaks at 2θ-values of 11.2±0.2°, 14.3±0.2°, 17.8±0.2°, 19.3±0.2°, 21.2±0.2°, 22.8±0.2° and 23.8±0.2°.

2. The crystalline composition according to claim 1, wherein said composition further has an X-ray powder diffraction pattern with peaks at 2θ-values of 12.6±0.2°, 16.7±0.2°, 18.4±0.2°, 20.0±0.2°, 20.4±0.2° and 28.0±0.2°.

3. The crystalline composition according to claim 1, wherein said composition further has an X-ray powder diffraction pattern with peaks at the following interplanar crystal spacing values of 7.9±0.2 Å, 6.2±0.2 Å, 5.0±0.2 Å, 4.6±0.2 Å, 4.2±0.2 Å, 3.9±0.2 Å and 3.7±0.2 Å.

4. The crystalline composition according to claim 3, wherein said composition further has an X-ray powder diffraction pattern with peaks at the following interplanar crystal spacing values of 7.1±0.2 Å, 5.3±0.2 Å, 4.8±0.2 Å, 4.4±0.2 Å, 4.3±0.2 Å and 3.2±0.2 Å.

5. The crystalline composition according to claim 1, wherein said composition has an infrared absorption spectrum with peaks at wavenumbers of 3255±5 cm$^{-1}$, 1742±5 cm$^{-1}$, 1604±5 cm$^{-1}$, 1539±5 cm$^{-1}$, 1398±5 cm$^{-1}$, 1302±5 cm$^{-1}$, 1198±5 cm$^{-1}$, 1124±5 cm$^{-1}$, 1032±5 cm$^{-1}$, 897±5 cm$^{-1}$, 804±5 cm$^{-1}$, 600±5 cm$^{-1}$ and 479±5 cm$^{-1}$.

6. The crystalline composition according to claim 3, wherein said composition further has an infrared absorption spectrum with peaks at wavenumbers of 3255±5 cm$^{-1}$, 1742±5 cm$^{-1}$, 1604±5 cm$^{-1}$, 1539±5 cm$^{-1}$, 1398±5 cm$^{-1}$, 1302±5 cm$^{-1}$, 1198±5 cm$^{-1}$, 1124±5 cm$^{-1}$, 1032±5 cm$^{-1}$, 897±5 cm$^{-1}$, 804±5 cm$^{-1}$, 600±5 cm$^{-1}$ and 479±5 cm$^{-1}$.

7. The crystalline composition according to claim 5, wherein said composition further has an infrared absorption spectrum with peaks at wavenumbers of 3441±5 cm$^{-1}$, 3116±5 cm$^{-1}$, 2938±5 cm$^{-1}$, 1500±5 cm$^{-1}$ and 1099±5 cm$^{-1}$.

8. The crystalline composition according to claim 1, wherein said composition has a differential scanning calorimetry pattern with an exothermic peak at 269.6±0.5° C.

9. The crystalline composition according to claim 1, wherein said composition is prepared by a process comprising the following steps of:
   providing ceftriaxone sodium raw material and sulbactam sodium raw material;
   separately grinding each of said raw materials to form particles having a median particle diameter of 25-88 μm; and
   mixing said grinded raw materials to give said composition.

10. The crystalline composition according to claim 9, wherein said median particle diameter has a values of 25-47 μm, 38-62 μm, or 58-88 μm.

11. A pharmaceutical formulation comprising the crystalline composition according to claim 1.

12. A pharmaceutical formulation comprising the crystalline composition according to claim 9.

13. The pharmaceutical formulation according to claim 11, wherein said pharmaceutical formulation is a powder for injection or an injection solution.

14. The pharmaceutical formulation according to claim 13, wherein said pharmaceutical formulation is a sterile powder for injection or a lyophilized powder for injection.

15. The pharmaceutical formulation according to claim 11, wherein said pharmaceutical formulation has a mass ratio of ceftriaxone-to-sulbactam of from 1:1 to 8:1.

16. The pharmaceutical formulation according to claim 15, wherein said pharmaceutical formulation has a mass ratio of ceftriaxone-to-sulbactam of from 1:1 to 4:1.

17. A method for treatment of a bacterial infection disease comprising administering a therapeutically effective amount of the pharmaceutical formulation according to claim 11 to a subject in need thereof.

18. The method according to claim 17, wherein said bacterial infection is caused by *Neisseria gonorrhoeae* having drug-resistance.

19. The method according to claim 18, wherein said drug-resistance is to a β-lactam antibacterial drug, a tetracycline antibacterial drug, a macrolide antibacterial drug, a fluoroquinolone antibacterial drug or an aminoglycoside antibacterial drug.

20. The method according to claim 17, wherein said bacterial infection disease is a urogenital system infection disease.

* * * * *